United States Patent [19]

Stapp

[11] 4,095,030

[45] June 13, 1978

[54] ISOMERIZATION OF DIACYLOXYOLEFINS

[75] Inventor: Paul R. Stapp, Bartlesville, Okla.

[73] Assignee: Phillips Petroleum Company, Bartlesville, Okla.

[21] Appl. No.: 761,083

[22] Filed: Jan. 21, 1977

[51] Int. Cl.$^2$ .................. C07C 67/28; C07C 69/02; C07C 69/16; C07C 69/78

[52] U.S. Cl. .................................. 560/100; 560/113; 560/262

[58] Field of Search .................. 260/476 R, 469, 491; 560/100, 113, 262

[56] References Cited

FOREIGN PATENT DOCUMENTS

| | | | |
|---|---|---|---|
| 2,454,768 | 5/1976 | Germany | 260/491 |
| 638,763 | 6/1950 | United Kingdom | 260/491 |

*Primary Examiner*—Jane S. Myers

[57] ABSTRACT

Diacyloxyolefins are isomerized by mixing one or more diacyloxyolefins with at least one alkali metal, alkaline earth metal or ammonium salt of a carboxylic acid and a polar diluent.

10 Claims, No Drawings

ISOMERIZATION OF DIACYLOXYOLEFINS

BACKGROUND OF THE INVENTION

The invention relates to the isomerization of diacyloxyolefins.

A very large variety of chemicals can be made from diolefins. One such group of chemicals is the diacyloxyolefins which are then easily converted to other various chemicals, such as the diols or glycols and the furans. As a specific illustration, 1,3-butadiene can be converted to 1,4-diacetoxy-2-butene and its isomer 1,2-diacetoxy-3-butene by various processes known in the art. The 1,4-isomer can be separated from the 1,2-isomer by fractional distillation as the 1,2-isomer is more volatile. The 1,4-isomer can then be hydrogenated to remove the double bond and to produce 1,4-diacetoxybutane which can then be converted to tetrahydrofuran by hydrolysis and cyclization. All of the above steps are well known in the art. It is readily apparent from the above illustration, however, that the overall process to produce tetrahydrofuran from 1,3-butadiene could be substantially improved by including an isomerization step to convert the 1,2-isomer to the 1,4-isomer. Although isomerization processes are known in the art that could be used to convert 1,2-diacetoxy-3-butene to 1,4-diacetoxy-2-butene, such processes generally require rather expensive catalysts that are useful for only a relatively short period of time. Besides producing tetrahydrofuran from 1,4-diacetoxy-2-butene, other chemicals such as diols or glycols also could be produced from various diacyloxyolefins and many such processes could likewise be improved by an effective or inexpensive diacyloxyolefin isomerization process.

Thus, an object of the invention is the isomerization of diacyloxyolefins.

Another object of the invention is an isomerization process that is both inexpensive and efficient in comparison to such processes known in the art.

These and other objects, aspects, and advantages of the present invention will be apparent to those skilled in the art from studying the specification and the appended claims.

SUMMARY OF THE INVENTION

A diacyloxyolefin is isomerized by mixing the olefin with a reagent selected from alkali metal, alkaline earth metal and ammonium salts of carboxylic acids and with a polar diluent having a dielectric constant of at least 10 and having no —OH groups. Such an isomerization system does not require the more expensive transition metal reagents as in the case of prior art systems and the mixture of the reagent and the diluent of the invention can be recovered and used again simply by direct distillation of the isomerized product from the reaction mixture.

DETAILED DESCRIPTION OF THE INVENTION

The instant invention is suitable for the isomerization of diacyloxyolefin compounds generally. Some suitable diacyloxyolefins are represented by the general formulas I and II shown below:

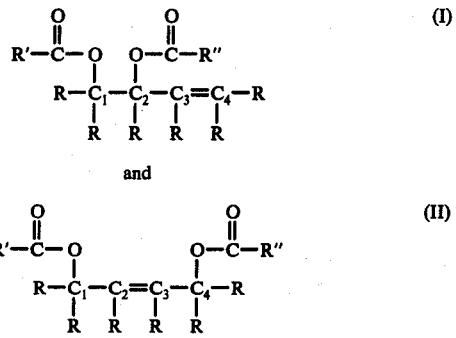

wherein R is hydrogen or an alkyl radical of from 1–4 carbon atoms, and wherein R' and R" can be the same or different and can be R or an aryl radical of from 6–10 carbon atoms, and wherein at least one of said R's attached to the carbon atoms numbered 1 and 4 in said formulas I and II is hydrogen.

The instant invention provides an isomerization system for converting diacyloxyolefins of general formula I to isomeric compounds of general formula II and vice versa. It is recognized of course, that the maximum extent of isomerization achieved according to the instant invention will be limited according to the equilibrium composition for said system assuming that no steps are taken to upset said equilibrium. The position of said equilibrium can generally be readily determined by following the extent of isomerization with time when starting with a single isomeric compound or preferably utilizing separately both isomers in two such runs.

Compounds represented by general formulas I and II above are often conveniently prepared by the oxidation of conjugated diolefins in the presence of carboxylic acids represented by the general formulas R'-CO$_2$H and R"-CO$_2$H wherein R and R" are as defined above as known in the art. Often in such processes mixtures of compounds I and II result.

The diacyloxyolefins suitable for use in the invention can be selected from a large variety of compounds. Some examples of compounds represented by general formula I which can be employed in the instant invention include 1,2-diacetoxy-3-butene, 1,2-diacetoxy-3-methyl-3-butene, 1,2-diformyloxy-3-butene, 1,2-dibenzoxy-3-butene, 1,2-di-1-naphthoyloxy-3-butene, 1,2-dipropionyloxy-3-butene, 1,2-diacetoxy-2,3-dimethyl-3-butene, 1-acetoxy-2-benzoxy-3-butene, 1-acetoxy-2-propionyloxy-3-methyl-3-butene. Some examples of compounds represented by general formula II which can be employed in the instant invention include 1,4-diacetoxy-2-butene, 1,4-diacetoxy-2-methyl-2-butene, 1,4-diformyloxy-2-butene, 1,4-dibenzoxy-2-butene, 1,4-dinaphthoyloxy-2-butene, 1,4-dipropionyloxy-2-butene, 1,4-diacetoxy-2,3-dimethyl-2-butene, 1-acetoxy-4-benzoxy-2-butene, 1-acetoxy-4-propionyloxy-2-methyl-2-butene.

Suitable mixtures, i.e., nonequilibrium mixtures, of isomeric compounds corresponding to formulas I and II can, of course, also be employed in the process of this invention. From a practical standpoint, it is envisioned that the instant invention will be of greatest benefit in the treatment of such mixtures. Further, the diacyloxyolefins most often employed in the invention will have the R' and R" groups the same.

The diacyloxybutenes are a preferred group of reactants with the diacetoxybutenes being especially preferred because of availability, reactivity and important utility.

The isomerization of the diacyloxyolefins described above is achieved according to the instant invention by use of a particular polar diluent/carboxylate salt reagent system employed substantially in the liquid phase as described below.

The polar diluent employed for the isomerization process of the instant invention must be substantially in the liquid phase under the reaction conditions, must have a dielectric constant of at least 10 when measured within the temperature range of 20–30° C., and must be free of —OH groups. It is noted that the isomerization reaction probably can be carried out in carboxylic acids but the reaction appears to be exceedingly slow. Furthermore, unless the carboxylic acid is the same as that from which the acyloxy

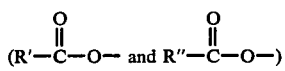

groups in the starting compound is derived, separation of the product mixture will be very difficult if not practically impossible. For these reasons carboxylic acids are not included within the scope of suitable diluents for the isomerization process of the instant invention.

Some examples of suitable diluents are shown below in Table I; however, it is emphasized that the diluents in Table I are merely illustrative and that Table I is not intended to be a complete compilation of suitable diluents.

Table I

| Diluent | Dielectric Constant at ° C. |
| --- | --- |
| Pyridine | 12.3 at 25° C. |
| 1-Methyl-2-pyrrolidinone | 32.2 at 25° C. |
| N,N-Dimethylformamide | 36.7 at 25° C. |
| N,N-Dimethylacetamide | 37.8 at 25° C. |
| Hexamethylphosphoramide | 30.5 at 20° C. |
| Benzonitrile | 25.2 at 25° C. |
| Acetonitrile | 36.2 at 25° C. |
| Dimethyl sulfoxide | 49 at 25° C. |
| Sulfolane | 44 at 30° C. |

The amount of said polar diluent employed is not particularly critical. Generally, the amount is in the range of from about 0.1 to about 20 liters per mole of starting diacyloxyolefin compound or mixture thereof; however, in the interest of economy and efficiency the amount of diluent can range from about 0.5 to about 5 liters per mole with good results.

The reagent utilized with the above polar diluent to isomerize said diacyloxyolefins is a compound selected from the group consisting of the alkali metal, alkaline earth metal, and ammonium salts of carboxylic acids wherein said carboxylic acid is represented by the general formulas

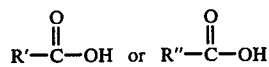

wherein R' and R" are as defined earlier. The term "alkali metal" is meant to denote the metals lithium, sodium, potassium, rubidium and cesium while the term "alkaline earth metal" is meant to denote the metals beryllium, magnesium, calcium, strontium, barium, zinc, cadmium and mercury.

Some examples of suitable compounds include sodium acetate, lithium formate, potassium benzoate, cesium propionate, ammonium acetate, sodium butyrate, potassium 1-naphthoate, beryllium acetate, magnesium formate, calcium benzoate, strontium acetate, barium acetate, zinc 1-naphthoate, cadmium butyrate, mercury (II) acetate and ammonium benzoate.

The amount of said carboxylate salt compound employed for the process of this invention is not believed to be critical and can be selected from a relatively broad range of amounts. Generally, the amount is within the range of from about 0.2 to about 20 moles per mole of starting diacyloxyolefin or mixture thereof, although in the interest of economy and efficiency the amount generally ranges from about 1 to about 5 moles per mole of diacyloxyolefin.

As noted earlier, generaly the R' and R" groups of the diacyloxyolefin are the same and in such cases it is readily apparent that the carboxylate salt reagent should correspond to the acyloxy group in the starting diacyloxyolefin or mixture thereof, i.e., the

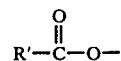

moiety in the carboxylate salt should be the same as that in the starting diacyloxyolefin. For example, an acetate salt should be used when a diacetoxyolefin is to be isomerized.

The diacyloxyolefin isomerization reaction of this invention is carried out at a temperature that can be selected over a broad range. Generally, the temperature ranges from about 130° to about 350° C. Based upon the results of the Examples hereinafter described, good results can be obtained employing a temperature ranging from about 175° C. to about 300° C.

The time utilized for said isomerization reaction will depend on temperature, catalyst concentration and the like and likewise on the extent of isomerization desired. In some instances, the reaction may be conducted for one minute or for as long as 24 hours and longer. Thus, in most instances, reaction time is not considered to be an especially significant parameter of the invention.

The isomerization reaction according to this invention is carried out at a pressure sufficient to maintain the diluent predominantly in the liquid phase which often is at autogenous pressure. Also, the reaction can be conducted in the presence of an added inert gas such as nitrogen at atmospheric or superatmospheric pressure. The latter condition may be required in those instances wherein a relatively low boiling diluent is used at a relatively high temperature in order to maintain a predominantly liquid phase system.

It is preferred, although it is not required, that the isomerization reaction mixture of this invention be homogeneous because of the ease of handling a homogeneous mixture as compared to a heterogeneous mixture. In any event, conventional liquid phase mixing procedures can be utilized during the reaction period in this invention.

The presence of water in the reaction mixture can give rise to the production of hydroxyolefin compounds which may be very difficult to separate from the diacyloxyolefins. For this reason it is preferred to operate under essentially anhydrous conditions. A convenient method for achieving this objective is to charge to the reaction mixture a suitable amount of carboxylic anhydride which corresponds to the

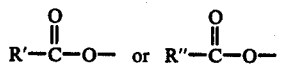

moiety present in the carboxylate salt reagent and the diacyloxyolefin. Any water present can then react with the carboxylic anhydride to form the carboxylic acid and thus effectively be eliminated from the reaction mixture.

It has also been found that a small amount of cyclic polyether compounds, commonly called crown ether compounds, can provide an enhancement of the diacyloxyolefin isomerization reaction rate when added to the reaction mixture containing the polar diluent and carboxylate salt reagent. Generally, the amount of the crown ether employed ranges from about 2 to about 400 millimoles per mole of the reagent previously described, i.e., carboxylic salt. The reason for said rate enhancement is not fully understood at present but may be related to the complexing ability of the crown ethers for the cation of the carboxylate salt reagent. A number of the crown ether compounds are commercially available such as 1,4,7,10,13,16-hexaoxacyclooctadecane, 2,3,11,12-dibenzo-1,4,7,10,13,16-hexaoxacyclooctadeca-2,11-diene and 2,3,11,12-dicyclohexyl-1,4,7,10,13,16-hexaoxacyclooctadecane.

The isomerization reaction mixture obtained according to the instant invention can often be subjected to a fractional distillation to provide a clean separation of the polar diluent and the respective isomeric diacyloxyolefins. When using a polar diluent that has appreciable water solubility it may be desirable to extract the reaction mixture with water and thereafter separate the diacyloxyolefin mixture by fractional distillation. Said water extraction should be conducted under conditions which do not promote hydrolysis of diacyloxyolefins, e.g., at temperatures below about 70° C. Furthermore, traces of water should be removed from the residual diacyloxyolefins before distillation in order to avoid hydrolysis. Other suitable separation methods can be employed in the separation of the reaction mixture components.

As mentioned earlier the instant invention can be employed to treat nonequilibrium mixtures of isomers of types I and II noted above to enrich said mixture in one or the other isomer depending on the starting composition of the mixture. Generally, the invention will find broadest utility in the isomerization of type I compounds to type II compounds. Type II compounds can be hydrogenated and cyclized to tetrahydrofurans or pyrrolidones. Alternatively, they can be hydrogenated then hydrolyzed to 1,4-diols which are useful as solvents or monomers in the preparation of polyesters or polyurethanes. Especially important in this regard is 1,4-butanediol which is employed in the production of polybutylene terephthalate an important polyester resin with highly desirable properties.

EXAMPLE I

Two runs were conducted according to the instant invention. In Run 1 the starting diacyloxyolefin was trans-1,4-diacetoxy-2-butene while in Run 2 the starting compound was 1,2-diacetoxy-3-butene.

In each run the reaction was carried out under nitrogen in a 100 ml three-necked flask equipped with a stirrer, thermometer, and condenser. The reaction flask was charged in each run with 50 ml sulfolane, 5 g (50 mmol) of fused anhydrous sodium acetate and 5.2 g (30 mmol) of the diacetoxybutene noted above. Each reaction mixture was refluxed for 7 hours during which time the temperature decreased from 278°–253° C.

Each reaction mixture was mixed with 250 ml water and the mixture extracted with four 50 ml portions of ether. The combined ether extracts were washed with two 50 ml portions of water, dried over $MgSO_4$, filtered, and the ether removed under vacuum in a rotary evaporating flask. The residues were weighed and analyzed by gas-liquid phase chromatography (GLC). The results of these runs are presented in Table II below.

Table II

| Run No. | Diacetoxybutenes Recovered, g. | Composition (GLC) of Recovered Diacetoxybutenes, %[a] | |
|---|---|---|---|
| 1 | 4.8 | 3,4-diacetoxy-1-butene | 27.8 |
|   |     | cis + trans-1,4-diacetoxy-2-butene | 68.5 |
| 2 | 5.1 | cis + trans-1,4-diacetoxy-2-butene | 48.9 |
|   |     | 3,4-diacetoxy-1-butene | 49.2 |

[a]The remainder of the sample is ether residue.

The above results demonstrate that extensive isomerization of the starting compounds occurred employing the isomerization system of the instant invention.

EXAMPLE II

Another run was carried out according to the invention employing the same type of vessel as that employed in the runs of Example I. In this run the flask was charged with 40 ml of hexamethylphosphoramide, 5 g (50 mmole) of fused anhydrous sodium acetate and 5.2 g (30 mmole) of 1,2-diacetoxy-3-butene. The reaction mixture was refluxed at 210° C. with stirring for 3 hours. The reaction mixture was treated in the same manner used in the runs of Example I to recover the diacetoxybutenes (5.3 g). Analysis (GLC) of the residue after the ether was removed indicated 59.3% starting compound, 2.3% cis-1,4-diacetoxy-2-butene and 15.8% trans-1,4-diacetoxy-2-butene. The balance of the product residue was apparently ether that had not been removed. The analysis shows that isomerization of the starting compound was achieved according to the invention.

EXAMPLE III

Another run was carried out in the same type of vessel as used in the previous runs. In this run the flask was charged with 50 ml of distilled sulfolane, 5 g (50 mmole) of fused anhydrous sodium acetate, 0.5 g of 1,4,7,10,-13,16-hexaoxacyclooctadecane and 5.2 g (30 mmole) of a diacetoxybutene mixture whose composition (GLC) is shown in Table III below. The reaction mixture was refluxed with stirring at 252° C. for 2 hours. The reaction mixture was treated in the same manner as in previous runs to recover the diacetoxybutenes. The residue after evaporation of the ether weighed 5.6 g and was analyzed by GLC. The GLC results for the starting mixture and the product are presented below.

Table III

| Composition % by GLC | Starting[a,b] | Product[a,b] |
|---|---|---|
| 1,2-diacetoxy-3-butene | 75.7 | 47.7 |
| cis-1,4-diacetoxy-2-butene | 3.9 | 6.2 |
| trans-1,4-diacetoxy-2- | 4.7 | 29.1 |

Table III-continued

| Composition % by GLC | Starting[a,b] | Product[a,b] |
|---|---|---|
| butene | | |

[a] The starting material contained 13.5% of an impurity believed to be a bromoacetoxybutene and the product contained 8.8% of said impurity.
[b] The remainder of the sample is ether residue.

The results of Table III demonstrate extensive isomerization of the starting diacetoxybutene mixture was achieved according to the instant invention.

EXAMPLE IV

A control run was conducted in essentially the same manner as Run 1 of Example I except that the reaction mixture was heated at 125° C. for 7 hours. The reaction mixture was poured into water and thoroughly extracted with ether. The combined ether extracts were washed with saturated aqueous $Na_2CO_3$, dried over $MgSo_4$, filtered and the ether removed under vacuum in a rotary evaporating flask. The residue weighed 9.2 g and contained about 45% sulfolane. Analysis of the residue by GLC showed no evidence of diacetoxybutene isomerization. It is possible that an extended reaction period, i.e., several days, might have given some detectable isomerization under these conditions, but such a long reaction period would prohibit commercial consideration of the process under those process conditions.

What is claimed is:

1. A process comprising:
   producing a mixture by mixing at least one diacyloxyolefin represented by the general fomulas I and II as follows

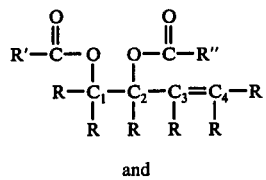

and

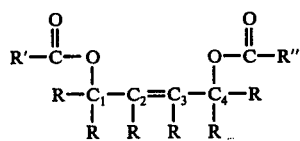

wherein R is hydrogen or an alkyl radical of from 1–4 carbon atoms, and wherein R' and R" can be the same or different and can be R or an aryl radical of from 6–10 carbon atoms, and wherein at least one of said R's attached to the carbon atoms numbered 1 and 4 in said formulas I and II is hydrogen; a reagent selected from the group consisting of an alkali metal, an alkaline earth metal and an ammonium salt of a carboxylic acid represented by the general formulas

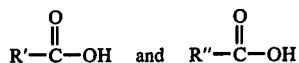

wherein R' and R" are as defined above, and a polar diluent having a dielectric constant of at least 10 when measured at a temperature ranging from 20° C. to 30° C. and having no —OH groups so that the diacyloxyolefin is isomerized wherein the mixture is under sufficient pressure to maintain the mixture predominantly in the liquid phase.

2. The process of claim 1 wherein the amount of reagent employed ranges from about 0.2 to about 20 moles per mole of diacyloxyolefin and the amount of diluent employed ranges from about 0.1 to about 20 liters per mole of diacyloxyolefin.

3. The process of claim 1 wherein the amount of reagent employed ranges from about 1 to 5 moles per mole of diacyloxyolefin and the amount of diluent employed ranges from about 0.5 to 5 liters per mole of diacyloxyolefin.

4. The process of claim 1 wherein the temperature of the mixture ranges from about 130° C. to about 350° C.

5. The process of claim 1 wherein the temperature of the mixture ranges from about 175° C. to about 300° C.

6. The process of claim 1 wherein the mixture further comprises from about 2 to about 400 millimoles crown ether per mole of reagent.

7. The process of claim 1 wherein the diacyloxyolefin is selected from the group consisting of 1,2-diacetoxy-3-butene, 1,2-diacetoxy-3-methyl-3-butene, 1,2-diformyloxy-3-butene, 1,2-dibenzoxy-3-butene, 1,2-di-1-naphthoyloxy-3-butene, 1,2-dipropionyloxy-3-butene, 1,2-diacetoxy-2,3-dimethyl-3-butene, 1-acetoxy-2-benzoxy-3-butene, 1-acetoxy-2-propionyloxy-3-methyl-3-butene, 1,4-diacetoxy-2-butene, 1,4-diacetoxy-2-methyl-2-butene, 1,4-diformyloxy-2-butene, 1,4-dibenzoxy-2-butene, 1,4-dinaphthoyloxy-2-butene, 1,4-dipropionyloxy-2-butene and 1,4-diacetoxy-2,3-dimethyl-2-butene, 1-acetoxy-4-benzoxy-2-butene, 1-acetoxy-4-propionyloxy-2-methyl-2-butene.

8. The process of claim 1 wherein the reagent is selected from the group consisting of sodium acetate, lithium formate, potassium benzoate, cesium propionate, ammonium acetate, sodium butyrate, potassium 1-naphthoate, beryllium acetate, magnesium formate, calcium benzoate, strontium acetate, barium acetate, zinc 1-naphthoate, cadmium butyrate, mercury (II) acetate and ammonium benzoate.

9. The process of claim 1 wherein the diluent is selected from the group consisting of pyridine, 1-methyl-2-pyrrolidinone, N,N-dimethylformamide, N,N-dimethylacetamide, hexamethylphosphoramide, benzonitrile, acetonitrile, dimethyl sulfoxide and sulfolane.

10. The process of claim 6 wherein the crown ether is selected from the group consisting of 1,4,7,10,13,16-hexaoxacyclooctadecane, 2,3,11,12-dibenzo-1,4,7,10,13,16-hexaoxacyclooctadeca-2,11-diene and 2,3,11,12-dicyclohexyl-1,4,7,10,13,16-hexaoxacyclooctadecane.

* * * * *